United States Patent [19]

Olsson et al.

[11] Patent Number: 5,140,015
[45] Date of Patent: Aug. 18, 1992

[54] 2-ARALKOXY AND 2-ALKOXY ADENOSINE DERIVATIVES AS CORONARY VASODILATORS AND ANTIHYPERTENSIVE AGENTS

[75] Inventors: Ray A. Olsson, Tampa; Robert D. Thompson, Riverview, both of Fla.

[73] Assignee: Whitby Research, Inc., Richmond, Va.

[21] Appl. No.: 482,282

[22] Filed: Feb. 20, 1990

[51] Int. Cl.$^5$ .................. A61K 31/00; C07H 19/00
[52] U.S. Cl. ........................... 514/46; 514/45; 536/24; 536/26
[58] Field of Search ............... 536/26, 24; 514/45, 514/46

[56] References Cited

U.S. PATENT DOCUMENTS 3,819,612  6/1974  Imai et al. .......................... 536/26

FOREIGN PATENT DOCUMENTS 0277917  8/1988  European Pat. Off. ............. 536/26
2460553  10/1975  Fed. Rep. of Germany ........ 546/26
101383  8/1975  Japan ................................. 536/26
7216299  6/1973  Netherlands ........................ 514/46
2203149  10/1988  United Kingdom .

OTHER PUBLICATIONS

J. Takeda Res. Lab., vol. 44, (Nos. 3/4), pp. 220–230, 1985.
Chem. Pharm. Bull., vol. 23, pp. 759–774, (1975).

Primary Examiner—Johnnie R. Brown
Assistant Examiner—James O. Wilson
Attorney, Agent, or Firm—Walter A. Hackler; Richard J. Hammond

[57] ABSTRACT

Compounds are disclosed having the formulae:

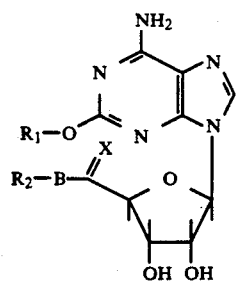

wherein $R_1$ is selected from the group, consisting of radicals represented by the general formulae:

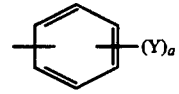

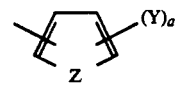

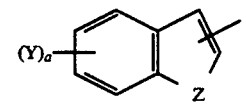

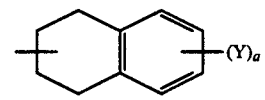

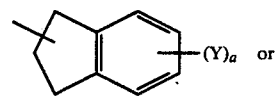

or

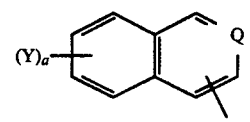

wherein Y is selected from the group consisting of lower alkyl, lower alkoxy, and halogen; Z is oxygen, sulfur or —NH, Q is —CH or nitrogen; a is zero or an integer of from one to three; and wherein, $R_2$ is selected from the group consisting of hydrogen and straight chain, branched and cyclic hydrocarbyl radicals having from one to four carbon atoms, and optionally substituted with a hydroxyl radical; and wherein X is two hydrogen atoms or oxygen and B is selected from oxygen and nitrogen, and pharmaceutically acceptable salts thereof, with the proviso that when X is two hydrogen atoms, B is oxygen, and with the further proviso that when B is oxygen then $R_1$ cannot be a phenyl or a substituted phenyl radical. Pharmaceutical preparations using these compounds and a method for inducing an adenosine response mediated by the adenosine $A_2$ receptor by administering these compounds are also disclosed.

16 Claims, No Drawings

2-ARALKOXY AND 2-ALKOXY ADENOSINE DERIVATIVES AS CORONARY VASODILATORS AND ANTIHYPERTENSIVE AGENTS

BACKGROUND OF THE INVENTION

1. Field of the Invention

The present invention is directed to certain 2-substituted adenosine derivatives which have beneficial cardiovascular and antihypertensive activity in mammals, including humans and domestic animals. The present invention is also directed to a process for making said compounds.

2. Brief Description of the Prior Art

Adenosine has been known for a long time to possess certain cardiovascular, and particularly coronary dilator activity. In an effort to obtain adenosine analogs of greater potency, or longer duration of activity, or both, many analogs of this naturally occurring nucleoside have been synthesized and tested.

Moreover, numerous studies have been conducted in order to elucidate the biochemical mechanism of action of adenosine and its analogs, and several theories and hypotheses have been proposed regarding biochemical pathways and receptor sites.

For discussion of current theories regarding the foregoing, reference is made to the following articles and publications: Adenosine Receptors: Targets for Future Drugs, by John W. Daly, Journal of Medicinal Chemistry, 25, 197 (1982); Cardiovascular Effects of Nucleoside Analogs, by Herman H. Stein and Pitambar Somani, Annals New York Academy of Sciences, 225, 380 (1979); Coronary Dilatory Action of Adenosine Analogs: a Comparative Study, by G. Raberger, W. Schutz and O. Kraupp. Archives internationales de Pharmacodynamie et de Therpie 230, 140-149 (1977); chapter 6 of the book titled: Regulatory Function of Adenosine, (pages 77-96), R. M. Berne, T. W. Rall and R. Rubio editors, Martinus Nijhoff publishers, The Hague/Boston/London; and Ethyl Adenosine-5'-carboxylate. A Potent Vasoactive Agent in the Dog, by Herman H. Stein, Journal of Medicinal Chemistry, 16, 1306 (1973); Modification of the 5' Position of Purine Nucleosides. 2. Synthesis and Some Cardiovascular Properties of Adenosine-5'(N-substituted)carboxamides, by Raj. N. Prasad et al., Journal of Medicinal Chemistry, 23 313 (1980), and Modification of the 5' Position of Purine Nucleosides. 1. Synthesis and Biological Properties of Alkyl Adenosine-5'-carboxylates by Raj N. Prasad et al., Journal of Medicinal Chemistry, 19, 1180 (1976).

Still more adenosine derivatives having beneficial cardiovascular activity are described in another application for United States Letters Patent of the present inventors, Ser. No. 601,435, filed on Apr. 18, 1984, now abandoned, Ser. No. 742,565, filed on Jun. 12, 1985, and Ser. No. 625,450, filed on Jun. 28, 1984.

Adenosine receptors have been subdivided into two subtypss: $A_1$ receptors, which inhibit adenylate cyclase, and $A_2$ receptors, which stimulate adenylate cyclase. It is thought that coronary vasodilation is mediated by $A_2$ receptor activation [see, e.g., Haleen, S., et. al., Life Sci., 36, 127-137 (1985)]. In order to minimize side effects associated with activation of $A_1$ receptors, it is a goal of pharmaceutical research to identify compounds highly selective for $A_2$ receptors.

Among a series of related compounds, one early compound claimed to possess coronary vasodilatory activity was 2-phenylaminoadenosine (CV-1808) [see Marumoto, R., et. al., Chem. Pharm. Bull., 23, 759 (1975)]. More recently, a series of $N^6$-substituted adenosine derivatives were disclosed as having high $A_2$ affinity and selectivity [see Trivedi, B. K., et. al., J. Med. Chem., 31, 271-273 (1988), and Bridges, A., et. al., J. Med. Chem., 31, 1282-1285 (1988)]. Another series of 2,5'-disubstituted adenosine derivatives have been disclosed as $A_2$ agonists (European Patent Application EP-277-917-A).

Many of the known adenosine derivatives are less than satisfactory as theraupeutics agents, due to low activity, short duration of effect, toxicity or undesirable side effects. In this light, there is a continuing interest in identifying agents which possess an desired profile of highly selective and potent adenosine $A_2$ receptor activity with minimal toxicity. The compounds of the present invention constitute a step in this direction.

SUMMARY OF THE INVENTION

There have now been discovered certain novel compounds having activity as $A_2$ adenosine receptor agonists and having the structural formula:

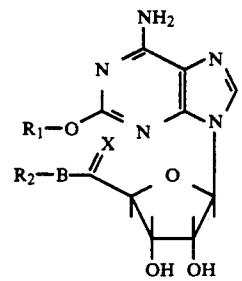

wherein $R_1$ is selected from the group, consisting of branched, straight-chained or cyclic hydrocarbyl radicals, having from one to six carbon atoms, and radicals represented by the general formulae:

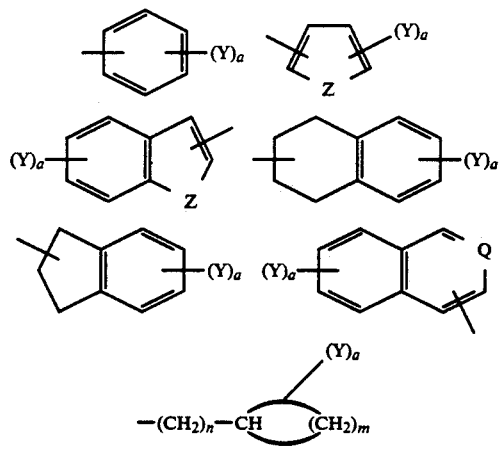

wherein Y is selected from the group consisting of lower alkyl, lower alkoxy, carboxy-lower alkyl and halogen; Z is oxygen, sulfur or —NH, Q is —CH or nitrogen; a is zero or an integer of from one to three; n is zero or an integer of from one to three; and m is an integer of from three to six; and wherein, when $R_1$ is a hydrocarbyl radical, it may be substituted with one or two radicals represented by the above general formula or substituted with —$OR_3$, wherein $R_3$ is hydrogen or lower alkyl, having from one to ten carbon atoms; $R_2$ is selected from the group consisting of hydrogen and straight chain, branched and cyclic hydrocarbyl radicals having from one to four carbon atoms, and optionally substituted with a hydroxyl radical; and wherein X is two hydrogen atoms or oxygen and B is selected from oxygen and nitrogen, with the proviso that when X is two hydrogen atoms, B is oxygen, and with the further proviso that when $R_3$ is present or $R_1$ is a branched or straight-chained hydrocarbyl radical, then $R_1$ must be substituted with one of the above radicals, and with the still further proviso that when B is oxygen, then $R_1$ cannot be a phenyl or a substituted phenyl radical.

DETAILED DESCRIPTION OF THE INVENTION

Certain derivatives of adenosine have been found in accordance with the present invention to selectively activate $A_2$ adenosine receptors and to possess significant cardiovascular and/or vasodilatory anti-hypertensive activity. The compounds used in the present invention are selected from the group of stereoisomers or mixtures thereof of compounds having activity as adenosine $A_2$ receptor agonists are represented by the formula:

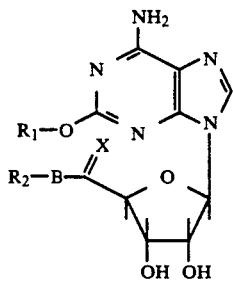

wherein $R_1$ is selected from the group, consisting of branched, straight-chained or cyclic hydrocarbyl radicals, having from one to six carbon atoms, and radicals represented by the general formulae:

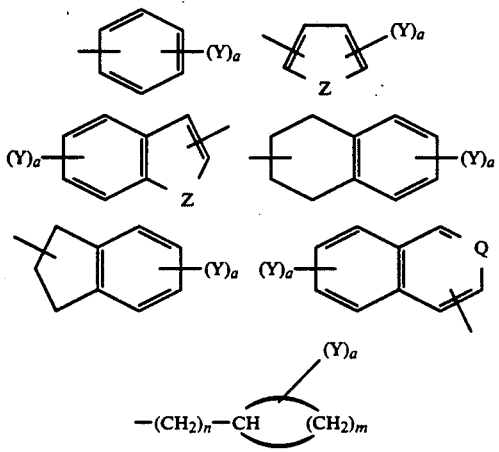

wherein Y is selected from the group consisting of lower alkyl, lower alkyl, carboxy-lower alkyl and halogen; Z is oxygen, sulfur or —NH; Q is —CH or nitrogen; a is zero or an integer of from one to three; n is zero or an integer of from one to three; and m is an integer of from three to six; and wherein, when $R_1$ is a hydrocarbyl radical, it may be substituted with one or two radicals represented by the above general formula or substituted with —$OR_3$, wherein $R_3$ is hydrogen or lower alkyl, having from one to ten carbon atoms; $R_2$ is selected from the group consisting of hydrogen and straight chain, branched and cyclic hydrocarbyl radicals having from one to four carbon atoms, and optionally substituted with a hydroxyl radical; and wherein X is two hydrogen atoms or oxygen and B is selected from oxygen and nitrogen, with the proviso that when X is two hydrogen atoms, B is oxygen, and with the further proviso that when $R_3$ is present or $R_1$ is a branched or straight-chained hydrocarbyl radical, then $R_1$ must be substituted with one of the above radicals, and with the still further proviso that when B is oxygen, then $R_1$ cannot be a phenyl radical or a substituted phenyl radical.

As used herein, the term "lower" as in "lower alkyl" refers to compounds having from 1 to 10 carbon atoms. The preferred lower alkyl radicals have from 1 to 4 carbon atoms. As used herein, the term "halogen" refers to bromide, chloride, fluoride and iodide radicals. Compounds falling within the scope of this invention are as follows:

2-benzyloxyadenosine
2-(2-phenylethoxy)adenosine
2-(5-phenylpentoxy)adenosine
2-cyclopentyloxyadenosine
2-cyclohexyloxyadenosine
2-(2-phenylethoxy)-5'-(N-ethylcarboxamido)adenosine
2-[2-(4-fluorophenyl)ethoxy]-5'-(N-ethylcarboxamido)adenosine
2-(3-phenylpropoxy)adenosine
2-cyclohexylethoxyadenosine
2-(4-phenylbutoxy)adenosine
2-(3,4,5-trimethoxyphenylethoxy)adenosine
2-[2-(2-thienyl)ethoxy]adenosine
2-[2-(3-thienyl)ethoxy]adenosine
2-(4-phenylbutoxy)adenosine
2-(2-pyridylethoxy)adenosine
2-(2-cyclohexylethoxy)adenosine
2-[2-(2-methylphenyl)ethoxy]adenosine
2-[2-(2-methoxyphenyl)ethoxy]adenosine
2-[2-(3-methoxyphenyl)ethoxy]adenosine
2-[2-(4-methoxyphenyl)ethoxy]adenosine
2-[2-(4-fluorophenyl)ethoxy]adenosine
2-[2-(3-indolyl)ethoxy]adenosine
2-[2-(1-naphthyl)ethoxy]adenosine
2-[2-(2-naphthyl)ethoxy]adenosine
2-(2,2-diphenylethoxy)adenosine
2-(4-biphenylethoxy)adenosine
2-(4-aminophenylethoxy)adenosine
2-(4-hydroxyphenylethoxy)adenosine
2-(2-indanyloxy)adenosine
2-2R-(1,2,3,4-tetrahydronaphthyloxy)adenosine
2-2S-(1,2,3,4-tetrahydronaphthyloxy)adenosine
2-(2-phenyl-1-propoxy)adenosine
2-(-2-phenyl,2R-hydroxyethoxy)adenosine
2-(-2-phenyl,2S-hydroxyethoxy)adenosine
2-(-2-phenyl,2R-methoxyethoxy)adenosine 2-(-2-phenyl,2S-methoxyethoxy)adenosine
2-(2R-phenyl,1-butoxy)adenosine
2-(2S-phenyl,1-butoxy)adenosine
2-[(4-carboxyethylphenyl)ethyoxy]adenosine
2-[(2-butylphenyl)ethoxy]adenosine The invention is further illustrated by the following examples which are illustrative of various aspects of the invention, and are not intended as limiting the scope of the inventions defined by the appended claims.

The invention also encompasses a method of preparation of the subject compounds, pharmaceutical compositions of the subject compounds and a method for inducing an adenosine $A_2$ response by administering the subject compounds to a patient. The general method of preparation of the above compounds comprises the reaction of a 2-haloadenosine derivative shown below with an alkali metal salt of $R_1OH$.

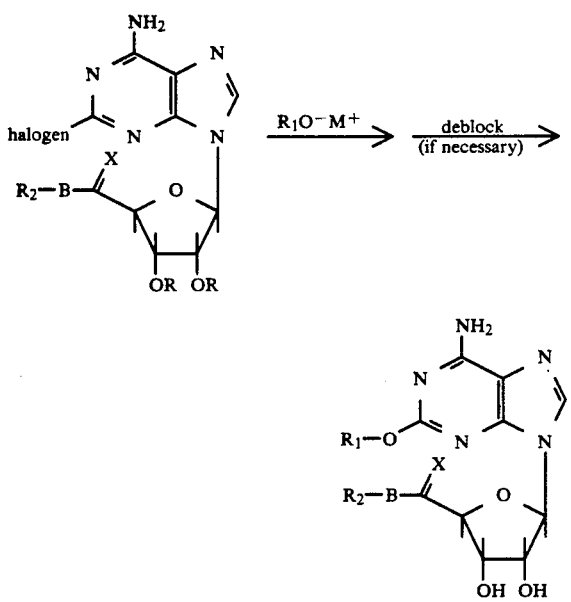

R = H, blocking group

Details of the synthesis, together with modifications and variations specifically tailored for particular compounds, are set out more fully in the specific examples which follow.

EXAMPLE 1

Preparation of 2-(3-phenyl-1-propoxy)adenosine

To a cold (10 C) solution of 3-phenyl-1-propanol (6 mL, 44.4 mmoles) and 70 mL of dry tetrahydrofuran was added n-butyllithium 1.6M in hexanes (25 mL, 40.0 mmoles) via syringe. The above solution was stirred for 15 minutes at room temperature followed by the addition of 2-chloro-2', 3'-O-isopropylideneadenosine (3.0 g, 8.8 mmoles). The mixture was refluxed for 4 days (HPLC showed less than 5% starting material). The solvents were removed in vacuo to give a dark brown syrup. Water (50 mL) was added and the pH adjusted to 7 with 4N HCl. The aqueous phase was extracted with ethyl acetate (4×50 mL) and the organic extracts dried over magnesium sulfate. The drying agent was filtered off and the solvents removed in vacuo to afford a brown syrup. This was purified by flash chromatography on silica gel (40–60μ) using a step gradient of chloroform to 2% methanol in chloroform. The fractions that showed product were collected and the solvents removed in vacuo to give a light brown syrup (blocked nucleoside). The syrup was dissolved in 80 mL of methanol. To this solution was added 10 mL water and 10 mL 98% formic acid and boiled until HPLC showed no blocked nucleoside. Sodium bicarbonate was added until a pH of 7 was achieved. The solvents were removed in vacuo. To the residue was added 2-propanol and the insoluble salts were filtered off. The 2-propanol was removed in vacuo and the product purified by preparative HPLC on a C-18 column, using a linear gradient of 50–70% methanol in water to yield 700 mg (20%) of a colorless solid. The characteristic NMR spectral peaks are: (60 MHz, DMSO-$d_6$) δ 1.95 (m, 2H), 2.63 (m, 2H), 3.5–5.4 (m, 8H), 4.15 (t, 2H), 5.78 (d, 2H), 7.20 (m, 7H), 8.15 (s, 1H). m.p. 100–102 C.

The above procedure was attempted using sodium hydride in place of n-butyllithium, which gave less than 5% yield by HPLC.

EXAMPLE 2

Preparation of 2-[2-(4-fluorophenyl)ethoxy]adenosine

The general procedure of Example 1 was followed, using the following reactants: 4-Fluorophenyl alcohol (4.2 mL, 33.5 mmoles); 1.6M n-butyllithium (20.0 mL, 31.9 mmoles); 2-chloro-2',3'-O-ethoxymethylideneadenosine (3.0 g, 8.4 mmoles). All conditions were identical with the exception of the hydrolysis and final purification conditions. Hydrolysis was achieved using concentrated acetic acid (5 mL). Final purification was done in the same manner, using a linear gradient of 50–68% methanol to yield 1.3 g (36%) of colorless solid. The characteristic NMR spectral peaks are: (60 MHz, DMSO-$d_6$) δ 3.12 (t, 2H), 3.55–5.55 (m, 8H), 4.58 (t, 2H), 5.88 (d, 1H), 7.05–7.41 (m, 6H), 8.08 (s, 1H). m.p. 148–150 C.

EXAMPLE 3

Preparation of 2-Cyclopentyloxyadenosine

The general procedure of Example was followed, using cyclopentanol in place of 3-phenyl-1-propanol. The characteristic NMR spectral peaks are: (60 MHz, DMSO-$d_6$) δ 1.80 (s, 8H), 3.50–5.48 (m, 9H), 5.80 (d, 1H), 7.20 (s, 2H), 8.14 (s, 1H). m.p. 147–150 C.

EXAMPLE 4

Preparation of 2-Cyclohexyloxyadenosine

The general procedure of Example 1 was followed, using cyclohexanol in place of 3-phenyl-1-propanol. The characteristic NMR spectral peaks are: (60 MHz, DMSO-$d_6$) δ 1.00–2.10 (m, 10H), 3.42–5.52 (m, 9H), 5.71 (d, 1H), 7.15 (s, 2H), 8.02 (s, 1H). m.p. 147 C.

EXAMPLE 5

Preparation of 2-(2-Cyclohexylethoxy)adenosine

The general procedure of Example was followed, using 2-cyclohexylethanol in place of 3-phenyl-1-propanol. The characteristic NMR spectral peaks are: (60 MHz, DMSO-$d_6$) δ 0.88–1.95 (m, 13H), 3.50–5.60 (m,8H), 4.64 (t, 2H), 5.89 (d, 1H), 7.20 (s, 2H), 8.10 (s, 1H). m.p. 185–187 C.

EXAMPLE 6

Preparation of 2-benzyloxyadenosine

The general procedure of Example was followed, using benzyl alcohol in place of 3-phenyl-1-propanol. The characteristic NMR spectral peaks are: (60 MHz, DMSO-$d_6$) δ 3.40–5.45 (m, 8H), 5.27 (s, 2H), 5.66 (d, 1H), 7.32 (m, 7H). 8.09 (s, 1H), m.p. 172–75 C.

EXAMPLE 7

Preparation of 2-(2-phenylethoxy)adenosine

The general procedure of Example 1 was followed, using phenethyl alcohol in place of 3-phenyl-1-propanol. The characteristic NMR spectral peaks are: (60 MHz, DMSO-$d_6$) δ 3.00 (t, 2H), 3.45–5.45 (m, 10H), 5.77 (d, 1H), 7.29 (s, 7H), 8.13 (s, 1H). m.p. 95–97 C.

EXAMPLE 8

Preparation of 2-[2-(2-methoxyphenyl)ethoxy]adenosine

The general procedure of Example 1 was followed, using 2-(2-methoxyphenyl)ethanol in place of 3-phenyl-1-propanol. The characteristic NMR spectral peaks are: (60 MHz, DMSO-$d_6$) δ 3.03 (t, 2H), 3.6–5.6 (m, 10H), 3.8 (s, 3H), 5.86 (d, 1H), 6.8–7.52 (m, 6H), 8.17 (s, 1H). m.p. 126–130 C.

EXAMPLE 9

Preparation of 2-[2-(3-methoxyphenyl)ethoxy]adenosine

The general procedure of Example 1 was followed, using 2-(3-methoxyphenyl)ethanol in place of 3-phenyl-1-propanol. The characteristic NMR spectral peaks are: (60 MHz, DMSO-$d_6$) δ 3.0 (t, 2H), 3.6–5.65 (m, 10H), 3.76 (s, 3H), 5.86 (d, 1H), 6.7–7.5 (m, 6H), 8.18 (s, 1H). m.p. 103–105 C.

EXAMPLE 10

Preparation of 2-[2-(4-methoxyphenyl)ethoxy]adenosine

The general procedure of Example was followed, using 2-(4-methoxyphenyl)ethanol in place of 3-phenyl-1-propanol. The characteristic NMR spectral peaks are: (60 MHz, DMSO-$d_6$) δ 2.95 (t, 2H), 3.5–5.52 (m, 8H), 3.74 (s, 3H), 4.4 (t, 2H), 5.86 (d, 1H), 6.86 (d, 2H), 7.25 (d, 2H), 7.33 (2, 2H), 8.2 (s, 1H).

EXAMPLE 11

Preparation of 2-[2-(2-methylphenyl)ethoxy]adenosine

The general procedure of Example was followed, using 2-methylphenylethanol in place of 3-phenyl-I-propanol. The characteristic NMR spectral peaks are: (60 MHz, DMSO-$d_6$) δ 2.33 (s, 3H), 3.04 (t, 2H), 3.5–5.55 (m, 8H), 4.45 (t, 2H), 5.85 (d, 1H), 7.2 (s, 4H), 7.3 (s, 2H), 8.19 (s, 1H). m.p. 166–168 C.

EXAMPLE 12

Preparation of 2-[2-(3,4,5-trimethoxyphenyl)ethoxy]adenosine

The general procedure of Example 1 was followed, using 3,4,5-trimethoxyphenylethanol in place of 3-phenyl-1-propanol. The characteristic NMR spectral peaks are: (60 MHz, DMSO-$d_6$) δ 2.95 (t, 2H), 3.5–5.58 (m, 8H), 4.45 (t, 2H), 5.72 (d, 1H), 6.65 (s, 2H), 7.28 (s, 2H), 8.16 (s, 1H). m.p. 110–112 C.

EXAMPLE 13

Preparation of 2-[2-(2-thienyl)ethoxy]adenosine

The general procedure of Example was followed, using 2-(2-thienyl)ethanol in place of 3-phenyl-1-propanol. The characteristic NMR spectral peaks are: (60 MHz, DMSO-$d_6$) δ 3.19 (t, 2H), 3.5–5.5 (m, 8H), 4.44 (t, 2H), 5.8 (d, 1H), 6.88–7.43 (m, 5H), 8.26 (s, 1H). m.p. 104–106 C.

EXAMPLE 14

Preparation of 2-[2-(3-thienyl)ethoxy]adenosine

The general procedure of Example was followed, using 2-(3-thienyl)ethanol in place of 3-phenyl-1-propanol. The characteristic NMR spectral peaks are: (60 MHz, DMSO-$d_6$) δ 3.1 (t, 2H), 3.3–5.6 (m, 8H), 4.5 (t, 2H), 5.85 (d, 1H), 7.0–7.58 (m, 5H), 8.22 (s, 1H). m.p. 99–102 C.

EXAMPLE 15

Preparation of 2-[2-(1-naphthyl)ethoxy]adenosine

The general procedure of Example was followed, using 2-(1-naphthyl)ethanol in place of 3-phenyl-1-propanol. The characteristic NMR spectral peaks are: (60 MHz, DMSO-$d_6$) δ 3.45–5.5 (m, 10H), 4.5 (t, 3H), 5.84 (d, 1H), 7.42 (s, 2H), 7.35–8.38 (m, 7H), 8.2 (s, 1H). m.p. 125–130 C.

EXAMPLE 16

Preparation of 2-[2-(3-indolyl)ethoxy]adenosine

The general procedure of Example 1 was followed, using 2-(3-indolyl)ethanol in place of 3-phenyl-1-propanol. The characteristic NMR spectral peaks are: (60 MHz, DMSO-$d_6$) δ 3.24 (t, 2H), 3.52–3.58 (m, 8H), 4.54 (t, 2H), 5.88 (d, 1H), 6.9–7.7 (m, 7H), 8.12 (s, 1H), 10.12 (s, 1H). m.p. 138–140 C.

EXAMPLE 17

Preparation of 2-(2-phenyl-1-propoxy)adenosine

The general procedure of Example ! was followed, using 2-phenyl-1-propanol in place of 3-phenyl-1-propanol. The characteristic NMR spectral peaks are: (60 MHz, DMSO-$d_6$) δ 1.36 (d, 3H), 3.1–5.55 (m, 11H), 5.85 (d, 1H), 7.35 (s, 7H), 8.2 (s, 1H). m.p. 135 C.

EXAMPLE 18

Preparation of 2-[(2-[(2R)-phenyl-1-butoxy]adenosine

The general procedure of Example 1 was followed, using (2S)-phenyl-1-butanol in place of 3-phenyl-1-propanol. The characteristic NMR spectral peaks are: (60 MHz, DMSO-$d_6$) δ 0.82 (t, 3H), 1.7 (m, 2H), 3.0 (m, 1H), 3.45–5.5 (m, 8H), 4.4 (d, 2H), 5.82 (d, 1H), 7.32 (s, 6H), 8.16 (s, 1H). m.p. 155 C.

EXAMPLE 19

Preparation of 2-[(2S)-phenyl-1-butoxy]adenosine

The general procedure of Example 1 was followed, using (2S)-phenyl-1-butanol in place of 3-phenyl-1-propanol. The characteristic NMR spectral peaks are: (60 MHz, DMSO-$d_6$) δ 0.8 (t, 3H), 1.73 (m, 2H), 2.95 (m, 1H), 3.6–5.57 (m, 8H), 4.4 (d, 2H), 5.89 (d, 1H), 7.32 (s, 6H), 8.22 (s, 1H). m.p. 108–110 C.

EXAMPLE 20

Preparation of 2-(4-phenyl-1-butoxy)adenosine

The general procedure of Example 1 was followed, using 4-phenyl-1-butanol in place of 3-phenyl-1-propanol. The characteristic NMR spectral peaks are: (60 MHz, DMSO-$d_6$) δ 1.75 (m, 4H), 2.61 (m, 2H), 3.5–5.55 (m, 10H), 5.81 (d, 1H), 7.27 (s, 7H), 8.16 (s, 1H). m.p. 93–96 C.

EXAMPLE 21

Preparation of 2-(5-phenyl-1-pentoxy)adenosine

The general procedure of Example 1 was followed, using 5-phenyl-1-pentanol in place of 3-phenyl-1-propanol. The characteristic NMR spectral peaks are: (60 MHz, DMSO-$d_6$) δ 1.35–2.07 (m, 6H), 2.72 (t, 2H), 3.6–5.58 (m, 8H), 4.33 (t, 2H), 5.88 (d, 1H), 7.23 (s, 7H), 8.1 (s, 1H). m.p. 102–104 C.

EXAMPLE 22

Preparation of 2-(2-phenyl)ethoxy-5'-N-ethylcarboxamidoadenosine

To a mixture of 2-phenylethanol (3.14 mL, 26.3 mmoles) in dry tetrahydrofuran (50 mL) was added n-butyllithium (16.4 mL, 26.2 mmoles) dropwise. This mixture was allowed to stir 15 min. at room temperature. The 2-chloro-5'-N-ethylcarboxamidoadenosine (1.5 g, 4.38 mmoles) was added in one portion and the mixture refluxed for 72 hours. Water (50 mL) was added. The precipitate was filtered off and the filtrate extracted with ethyl acetate (4×50 mL). The organic phases were dried with magnesium sulfate. The drying agent was removed by filtration and the solvents removed in vacuo to give a foam. Purification on a preparative HPLC C-18 column, using a linear gradient of 50–70% methanol/water gave a colorless solid. The characteristic NMR spectal peaks are: (60 MHz, DMSO-$d_6$) δ 1.07 (t, 3H), 3.39 (m, 4H), 4.1-4.77 (m, 5H), 5.5–5.78 (m, 2H), 5.9 (d, 1H), 7.32 (s, 5H), 7.46 (s, 2H), 8.2 (s, 1H), 8.9 (t, 1H). m.p. 130–133 C.

EXAMPLE 23

Preparation of 2-(3-cyclohexyl)propoxyadenosine

The general procedure of Example I was followed, using 3-cyclohexyl-1-propanol in place of 3-phenyl-1-propanol. The characteristic NMR spectral peaks are: (60 MHz, DMSO-$d_6$) δ 0.7–1.9 (m, 15H), 3.55–5.55 (m, 10H), 5.8 (d, 1H), 7.23 (s, 2H), 8.14 (s, 1H).

EXAMPLE 24

Preparation of 2-[2-(2-naphthyl)ethoxy]adenosine

The general procedure of Example was followed, using 2-(2-naphthyl)ethanol in place of 3-phenyl-1-propanol. The characteristic NMR spectral peaks are: (60 MHz, DMSO-$d_6$) δ 3.3 (t, 2H), 3.42–5.5 (m, 8H), 4.67 (t, 2H), 5.84 (d, 1H), 7.22–8.05 (m, 7H), 7.89 (s, 2H), 8.18 (s, 1H).

EXAMPLE 25

Assays of the cardiovascular potency of the above compounds at the $A_1$ receptors of the SA node and at the $A_2$ receptor of the coronary artery employed perfused hearts from female Sprague-Dawley guinea pigs in an isolated Langendorff heart preparation. An assay consists of an infusion of a spectophotometrically standardized solution of test compound directly into the aortic cannula at rates increasing stepwise every 5 minutes. Collection of the total cardiac effluent during the first half of each infusion period provides a measure of coronary flow ($A_2$ effect). The concentration of test compound required to produce a half-maximal increase in coronary flow is determined. Registration of the ECG assesses the effect of the test compound on SA node (stimulus to Q interval, $A_1$ effect). The concentration of test compound required to produce a half-maximal prolongation of stimulus to Q interval is determined. Table I summarizes the resultant data, using adenosine as a reference compound. The ratio of $A_1$ and $A_2$ effects of test compounds are calculated to provide the selectivity ratio.

TABLE I

| Example | Coronary Blood Flow Increase ($A_2$) $EC_{50}$ (nM) | SQ Prolongation ($A_1$) $ED_{50}$ (nM) | Selectivity ($A_1/A_2$) |
| --- | --- | --- | --- |
| Adenosine | 49.7 | 3162 | 63.6 |
| 6 | 419.3 | 6310 | 15 |
| 7 | 2.8 | 19953 | 7126 |
| 3 | 91.7 | 79433 | 866 |
| 4 | 656.9 | 100000 | 152 |
| 22 | 1.3 | 14962 | 11509 |
| 1 | 61.3 | 19953 | 326 |
| 13 | 3.7 | 11885 | 3212 |
| 14 | 3.4 | 18836 | 5540 |
| 20 | 9.9 | 7356 | 743 |
| 15 | 5.1 | 8414 | 1650 |
| 17 | 9.0 | 53088 | 5899 |
| 12 | 22.0 | 47315 | 2151 |
| 5 | 1.0 | 8630 | 8630 |
| 11 | 3.8 | 25119 | 6610 |
| 9 | 2.6 | 16218 | 6238 |
| 18 | 373.7 | 18836 | 50 |
| 19 | 31.4 | 27384 | 872 |
| 8 | 32.0 | 35481 | 1109 |
| 21 | 6.4 | 4597 | 718 |
| 2 | 0.9 | 25606 | 29432 |
| 16 | 9.8 | 14125 | 1441 |
| 10 | 1.4 | 19724 | 14089 |
| 23 | 2.2 | 3758 | 1708 |
| 24 | 0.5 | 11416 | 22832 |

This data shows the high degree of potency and selectivity of the subject compounds in increasing coronary blood flow at low concentrations while having comparatively little effect on the SQ prolongation. The ratios calculated show the marked $A_2$ selectivity of the subject compounds.

It is essential that the compounds herein be capable of binding selectively to $A_2$ adenosine receptors, e.g., in a human. 2-phenylethoxy-5'-(N-ethylcarboxamido)adenosine and 2-(4-fluorophenyl)ethoxyadenosine 2-[2-(4-methoxyphenyl) ethoxy]adenosine and 2-[2-(2-naphthyl) ethoxy]adenosine are particularly preferred compounds because of the high affinity and selectivity for $A_2$ adenosine receptors. It is believed that the compounds herein will be useful as cardiac vasodilators in humans and other animals.

Various modifications of the herein disclosed invention, in terms of structural modifications of the invented compounds and also in terms of making or using the same, may become readily apparent to those skilled in the art in light of the above disclosure. For example, the compounds of the present invention may be administered as pharmaceutically acceptable salts.

Inasmuch as the compounds of the present invention are useful as cardiac vasodilators, cardiovascular, and particularly as anti-hypertensive agents in mammals, domestic animals and humans, various modes of administering the compounds will be apparent to a person having average skill in the art. Such modes of administering the compounds include oral and topical administration, and intravenous infusion. One having average skill in the art may readily prepare suitable formulations for the abovementioned and other modes of administering the compounds of the invention.

In light of the foregoing, the scope of the present invention should be interpreted solely from the following claims, as such claims are read in light of the disclosure.

We claim:

1. A compound selected from the group of stereoisomers or mixtures thereof of compounds having the formulae:

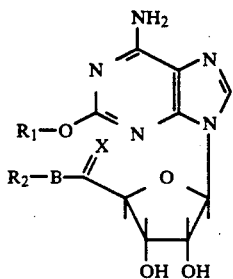

wherein $R_1$ is

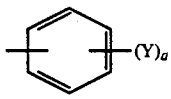

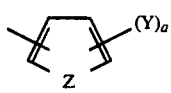

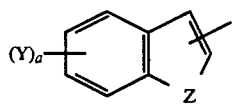

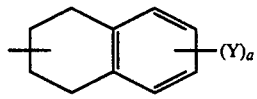

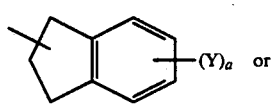 or

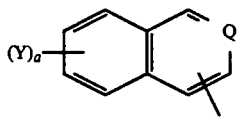

wherein Y is selected from the group consisting of lower alkyl, lower alkoxy, and halogen; Z is oxygen, sulfur or —NH, Q is —CH or nitrogen; a is an integer from 0 to 3; and wherein $R_2$ is selected from the group consisting of hydrogen and straight, branched or cyclic hydrocarbyl radicals having from 1 to 4 carbon atoms; and wherein x is 2 hydrogen atoms or oxygen and B is selected from the group consisting of oxygen and nitrogen, with the proviso that when x is 2 hydrogen atoms, B is oxygen and with the further proviso that when B is oxygen then $R_2$ cannot be a phenyl or phenyl substituted with one or more substituents at positions 2-, 3-, 4- and 5-.

2. A compound of claim 1 wherein a is zero.
3. A compound of claim 1 wherein Y is halogen.
4. A compound of claim 1 wherein Q is —CH.
5. A compound of claim 1 wherein $R_1$ is phenylethyl.
6. A compound of claim 1 wherein $R_1$ is 4-fluorophenylethyl.
7. A compound of claim 1 wherein $R_1$ is 4-methoxyphenylethyl.
8. A compound of claim 1 wherein $R_1$ is 2-(2-naphthyl)ethyl.
9. A compound of claim 1 wherein $R_2$ is ethyl and $R_1$ is phenylethyl.
10. 2-(2-phenyl)ethoxyadenosine.
11. 2-(2-phenyl)ethoxy-5'-N-ethylcarboxamidoadenosine.
12. 2-[2-(4-fluorophenyl)ethoxy]adenosine.
13. 2-[2-(4-methoxyphenyl)ethoxy]adenosine.
14. 2-[2-(2-naphthyl)ethoxy]adenosine.
15. 2-(2-cyclohexyl)ethoxyadenosine.
16. A method for inducing an adenosine response indicated by an adenosine $A_2$ receptor in a human or animal, comprising the step of administering to a human or an animal in need of such treatment, an effective amount of a compound having the formulae:

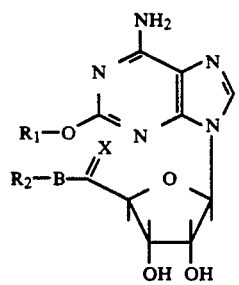

wherein $R_1$ is

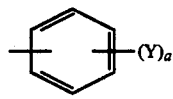

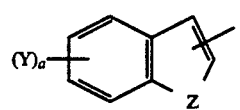

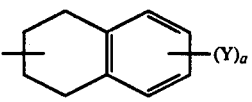

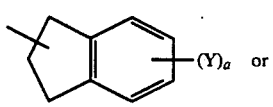

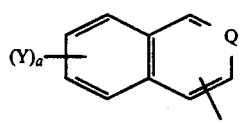

wherein Y is selected from the group consisting of lower alkyl, lower alkoxy, and halogen; Z is oxygen, sulfur or —NH, Q is —CH or nitrogen; a is an integer from 0 to 3; and wherein $R_2$ is selected from the group consisting of hydrogen and straight, branched or cyclic hydrocarbyl radicals having from 1 to 4 carbon atoms; and wherein x is 2 hydrogen atoms or oxygen and B is selected from the group consisting of oxygen and nitrogen, with the proviso that when X is 2 hydrogen atoms, B is oxygen with the further proviso that when B is oxygen then $R_2$ cannot be a phenyl or phenyl substituted with one or more substituents at positions 2-, 3-, 4- and 5-.

* * * * *